United States Patent
Altman et al.

(10) Patent No.: US 7,601,511 B2
(45) Date of Patent: Oct. 13, 2009

(54) BIOTIN-FACILITATED TRANSPORT IN GRAM NEGATIVE BACTERIA

(75) Inventors: Elliot Altman, Athens, GA (US);
Jennifer R. Walker, Bogart, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 10/579,248

(22) PCT Filed: Nov. 12, 2004

(86) PCT No.: PCT/US2004/037896

§ 371 (c)(1),
(2), (4) Date: Feb. 28, 2007

(87) PCT Pub. No.: WO2005/046730

PCT Pub. Date: May 26, 2005

(65) Prior Publication Data

US 2007/0265186 A1    Nov. 15, 2007

Related U.S. Application Data

(60) Provisional application No. 60/519,100, filed on Nov. 12, 2003.

(51) Int. Cl.
*C12Q 1/02*    (2006.01)
*C12Q 1/18*    (2006.01)

(52) U.S. Cl. .......................................... 435/29; 435/32

(58) Field of Classification Search ...................... None
See application file for complete search history.

(56) References Cited

U.S. PATENT DOCUMENTS

| | | | |
|---|---|---|---|
| 5,108,921 | A | 4/1992 | Low et al. |
| 5,416,016 | A | 5/1995 | Low et al. |
| 5,635,382 | A | 6/1997 | Low et al. |
| 5,688,488 | A | 11/1997 | Low et al. |
| 5,820,847 | A | 10/1998 | Low et al. |
| 5,976,535 | A | 11/1999 | Fritzberg et al. |
| 6,306,993 | B1 | 10/2001 | Rothbard et al. |
| 6,322,788 | B1 * | 11/2001 | Kim .................... 424/164.1 |
| 6,451,971 | B1 | 9/2002 | Akiyama et al. |
| 6,495,663 | B1 | 12/2002 | Rothbard et al. |
| 6,624,140 | B1 | 9/2003 | Abraham et al. |
| 7,033,594 | B2 | 4/2006 | Low et al. |
| 2002/0131965 | A1 | 9/2002 | Rothbard et al. |
| 2003/0162719 | A1 | 8/2003 | Rothbard et al. |
| 2004/0049011 | A1 | 3/2004 | Abraham et al. |
| 2005/0136008 | A1 | 6/2005 | Elmaleh et al. |
| 2006/0111274 | A1 | 5/2006 | Rothbard et al. |

FOREIGN PATENT DOCUMENTS

| CA | 2 545 679 A1 | 5/2005 |
|---|---|---|
| DE | 100 55 789 A1 | 6/2002 |
| EP | 1 036 798 A1 | 9/2000 |
| EP | 1 036 798 B1 | 7/2003 |
| WO | 90/12096 * | 10/1990 |
| WO | WO 90/12096 A1 | 10/1990 |
| WO | WO 95/31556 A1 | 11/1995 |
| WO | 98/52614 * | 11/1998 |
| WO | WO 98/52614 A2 | 11/1998 |
| WO | WO 98/52614 A3 | 11/1998 |
| WO | WO 99/06440 A1 | 2/1999 |
| WO | WO 02/40511 A2 | 3/2002 |
| WO | WO 02/40511 A3 | 3/2002 |
| WO | WO 2005/032598 A1 | 4/2005 |
| WO | WO 2005/046730 A2 | 5/2005 |
| WO | WO 2005/046730 A3 | 5/2005 |

OTHER PUBLICATIONS

American Type Culture Collection, "ATTC No. 9721," organism: *Pseudomonas aeruginosa* Migula; designation: NRS 112 [online]; Manassas, VA [retrieved on Feb. 23, 2007]. Retrieved from the Internet: <http://www.atcc.org/common/catalog/numSearch/numResults.cfm?atccNum=9721&CFID=10430581&CFTOKEN=76dd390cc23da4a9-DB0128C2-92C7-CF98-64C2BC85A22D7B2D>; 2 pgs.

American Type Culture Collection, "ATTC No. 25923," organism: *Staphylococcus aureus* Rosenbach; designation: Seattle 1945 [online]; Manassas, VA [retrieved on Feb. 23, 2007]. Retrieved from the Internet: <http://www.atcc.org/common/catalog/numSearch/numResults.cfm?atccNum=25923&CFID=10430581&CFTOKEN=76dd390cc23da4a9-DB0128C2-92C7-CF98-64C2BC85A22D7B2D>; 4 pgs.

Fickel et al., "Transport of impermeant substances in *E. coli* by way of oligopeptide permease," *Nat. New Biol.*, 1973;241:161-163.

Hussey et al., "Efficient Delivery of Streptavidin to Mammalian Cells: Clathrin-Mediated Endocytosis Regulated by a Synthetic Ligand," *J. Am. Chem. Soc.*, 2002; 124:6265-6273;S1-S8.

Miller, *Experiments in Molecular Genetics*, Cold Spring Harbor Laboratory Press, Cold Spring Harbor, NY (1972).

Miller et al., "The design, synthesis and study of siderophore-antibiotic conjugates," *Biol. Met.*, 1991; 4:62-69.

Morley et al., "Backbone-modified analogues of small peptides: transport and antibacterial activity," *Biochem. Soc. Trans.*, 1983; 11:798-800.

Payne, "Peptides and micro-organisms," *Adv. Microb. Physiol.*, 1976; 13:55-113.

Payne, "Transport and utilization of peptides by bacteria," in *Microorganisms and Nitrogen Sources*, 1980; Title page, publication page and pp. 211-256.

Payne et al., "Peptide transport by micro-organisms," *Adv. Microb. Physiol.*, 1994; 36:1-80.

Piffeteau et al., "Biotin transport by a biotin-deficient strain of *Escherichia coli*," *Biochim. Biophys. Acta*, 1982; 688:29-36.

Piffeteau et al., "Biotin uptake: influx, efflux, and countertransport in *Escherichia coli*," *Biochim. Biophys. Acta*, 1985; 816:77-82.

Prakash et al., "Active transport of biotin in *Escherichia coli* K-12," *J. Bacteriol.*, 1974; 120(2):785-791.

(Continued)

*Primary Examiner*—Patricia A Duffy
(74) *Attorney, Agent, or Firm*—Mueting Raasch & Gebhardt, P.A.

(57) ABSTRACT

Biotinylation of compounds such as peptides and peptidomimetics facilitates illicit transport of the compounds into Gram negative bacteria.

18 Claims, 9 Drawing Sheets

OTHER PUBLICATIONS

Press et al., "A comparative evaluation of conventional and pretargeted radioimmunotherapy of CD20-expressing lymphoma xenografts," *Blood*, 2001; 98:2535-2543.

Schägger et al., "Tricine-sodium dodecyl sulfate-polyacrylamide gel electrophoresis for the separation of proteins in the range from 1-100 kDa," *Anal. Biochem.*, 1987; 166:368-379.

Scherrer et al., "Molecular sieving by the *Bacillus megaterium* cell wall and protoplast," *J. Bacteriol.*, 1971; 107:718-735.

Song et al., "Enhanced neuroprotective effects fibroblast growth factor in regional brain ischemia after conjugation to a blood-brain delivery vector," *J. Pharmacol. Exp. Ther.*, 2002;301(2):605-610.

Staskawicz et al., "Phaseolotoxin transport in *Escherichia coli* and *Salmonella typhimurium* via the oligopeptide permease," *J. Bacteriol.*, 1980; 142:474-479.

Walker, Jennifer Renee, "Improving the Stability of Bioactive Peptides Using Protein-Based Motifs," Ph.D. Dissertation, University of Georgia Department of Microbiology. Cover date: Dec. 2002. Publically available Oct. 23, 2003.

Walker et al., "Using protein-based motifs to stabilize peptides," *J. Peptide Research*, 2003; 62:214-226.

Walker et al., "Biotinylation facilitates the uptake of large peptides by *Escherichia coli* and other Gram-negative bacteria," *Applied and Environmental Microbiology*, 2005; 71(4):1850-1855.

Wittmann et al., "New synthetic siderophores and their β-lactam conjugates based on diamino acids and dipeptides," *Bioorg. Med. Chem.*, 2002; 10:1659-1670.

International Search Report and the Written Opinion of the Internation Searching Authority, dated Jul. 3, 2006. 22 pages.

International Preliminary Report on Patentability, dated Aug. 24, 2006. 13 pages.

Altman et al., "S Gene Product: Identification and Membrane Localization of a Lysis Control Protein," *J. Bacteriol.*, Sep. 1983; 155(3):1130-1137.

Ames et al., "Illicit Transport: The Oligopeptide Permease," *Proc. Natl. Acad. Sci. USA*, Feb. 1973; 70(2):456-458.

Ames et al., "Simple, Rapid, and Quantitative Release of Periplasmic Proteins by Chloroform," *J. Bacteriol.*, Dec. 1984; 160(3):1181-1183.

Atherton et al., "Phosphonopeptide Antibacterial Agents Related to Alafosfalin: Design, Synthesis, and Structure-Activity Relationships," *Antimicrob. Agents and Chemother.*, Dec. 1980; 18(6):897-905.

Barak et al., "Specialized Peptide Transport System in *Escherichia coli*," *J. Bact.*, Jun. 1975; 122(3):1200-1207.

Bodanszky et al., "Synthesis of Biocytin-Containing Peptides," *J. Am. Chem. Soc.*, Jan. 1977; 99(1):235-239.

Bonfils et al., "Uptake by Macrophages of a Biotinylated Oligo-α-deoxythymidylate by Using Mannosylated Streptavidin," *Bioconjug. Chem.*, Jul.-Aug. 1992; 3(4):277-284.

Campbell, "Sensitive Mutants of Bacteriophage λ," *Virology*, May 1961; 14:22-32.

Campbell et al., "A Mutant of *Escherichia coli* That Requires High Concentrations of Biotin," *Proc. Nat. Acad. Sci. USA*, Mar. 1972; 69(3):676-680.

Campbell et al., "Biotin Regulatory (bir) Mutations of *Escherichia coli*," *J. Bacteriol.*, Jun. 1980; 142(3)1025-1028.

Chen et al, "Increased Cellular Uptake of the Human Immunodeficiency Virus-1 Tat Protein after Modification with Biotin," *Analytical Biochemistry*, May 1995; 227:168-175.

Dargis et al., "Use of Biotinylated β-Lactams and Chemiluminescence for Study and Purification of Penicillin-Binding Proteins in Bacteria," *Antimicrobial Agents and Chemotherapy*, May 1994; 38(5):973-980.

Detmers et al., "Kinetics and Specificity of Peptide Uptake by the Oligopeptide Transport System of *Lactococcus lactis*," *Biochemistry*, Nov. 1998; 37:16671-16679.

Eisenberg et al., "Properties of α-Dehydrobiotin-Resistant Mutants of *Escherichia coli* K-12," *J. Bacteriol.*, Apr. 1975; 122(1):66-72.

Fall et al., "Analysis of bacterial biotin-proteins," *Biochim. Biophys. Acta*, Feb. 1975; 379(2):496-503.

Gilleland, Jr., et al., "Ultrastructural and Chemical Alteration of the Cell Envelope of *Pseudomonas aeruginosa*, Associated with Resistance to Ethylenediaminetetraacetate Resulting from Growth in a $Mg^{2+}$-Deficient Medium," *J. Bacteriol.*, Jan. 1974; 117(1):302-311.

Green, "Avidin 3. The Nature of the Biotin-Binding Site," *Biochem. Journal*, Dec. 1963; 89(3):599-609.

Guha, "Divergent Orientation of Transcription from the Biotin Locus of *Escherichia coli*," *J. Mol. Biol.*, Feb. 1971; 56:53-62.

Hofmann et al., "Avidin-Biotin Affinity Columns. General Methods for Attaching Biotin to Peptides and Proteins," *J. Am. Chem. Soc.*, May 1978; 100(11):3585-3590.

Ketner et al., "A Deletion Mutation Placing the Galactokinase Gene of *Escherichia coli* under Control of the Biotin Promoter," *Proc. Natl. Acad. Sci. USA*, Jul. 1974; 71(7):2698-2702.

Kinoshita et al., "Proton Motive Force Is Not Obligatory for Growth of *Escherichia coli*," *J. Bacteriol.*, Dec. 1984; 160(3):1074-1077.

Luckey et al., "Iron Uptake in *Salmonella typhimurium*: Utilization of Exogenous Siderochromes as Iron Carriers," *J. Bacteriol.*, Sep. 1972; 111(3):731-738.

Mah et al., "Nutritional Requirements of *Staphylococcus aureus* S-6," *Appl. Microbiol.*, Jul. 1967; 15(4):866-870.

Minko et al., "Enhancing the anticancer efficacy of camptothecin using biotinylated poly(ethyleneglycol) conjugates in sensitive and multidrug-resistant human ovarian carcinoma cells," *Cancer Chemother. Pharmacol.*, Aug. 2002; 50:143-50. Available on-line Jun. 11, 2002.

Naider et al., "Multiplicity of Oligopeptide Transport Systems in *Escherichia coli*," *J. Bacteriol.*, Jun. 1975; 122(3):1208-1215.

Nikaido et al., "Molecular Basis of Bacterial Outer Membrane Permeability," *Microbiol Rev.*, Mar. 1985; 49(1):1-32.

Nikaido, "Chapter 5: Outer Membrane," in *Escherichia coli and Salmonella Cellular and Molecular Biology*, $2^{nd}$ ed., vol. 1., ASM Press, American Society for Microbiology, Washington, D.C. 1996, Title page, publication page and pp. 29-47.

NNIS System Report, Special Articles, "National Nosocomial Infections Surveillance (NNIS) System Report, data summary from Jan. 1992 to Jun. 2002, issued Aug. 2002," Division of Healthcare Quality Promotion, National Center for Infectious Diseases, Centers for disease Control and Prevention, Public Health Service, US Department of Health and Human Services, Atlanta, GA, Nov. 2002, pp. 458-475.

Otvos, Jr. et al., "Interaction between Heat Shock Proteins and Antimicrobial Peptides," *Biochemistry*, Nov. 2000; 39(46):14150-14159. Available on-line Oct. 21, 2000.

Pai, "Biotin uptake in Biotin Regulatory Mutant of *Escherichia coli*," *J. Bacteriol.*, Oct. 1973; 116(1):494-496.

Pardridge, "Targeting Neurotherapeutic Agents Through the Blood-Brain Barrier," *Arch. Neurol.*, Jan. 2002; 59:35-40.

Payne et al., "Size Restriction on Peptide Utilization in *Escherichia coli*," *J. Biol. Chem*, Dec. 1968; 243(23):6291-6299.

Ramanathan et al., "Targeted PEG-based bioconjugates enhance the cellular uptake and transport of a HIV-1 TAT nonapeptide," *J. Control. Release*, Dec. 2001; 77(3):199-212.

Stolz et al., "Rapid purification of a functionally active plant sucrose carrier from transgenic yeast using a bacterial biotin acceptor domain," *FEBS Letters*, 1995; 377:167-171.

Wermuth et al., "Glossary of Terms used in Medicinal Chemistry (IUPAC Recommendations 1998)," [online]. International Union of Pure and Applied Chemistry, Chemistry and Human Health Division, Medicinal Chemistry Section (1998). [retrieved on Oct. 5, 2006]. Retrieved from the Internet:<URL:www.chem.qmul.ac.uk/iupac/medchem>; 2 pgs.

"Calcium Chloride" datasheet. CQ Concepts, Ringwood, Illinois, Jun. 15, 2007. Available online [retrieved on Jul. 15, 2008]. Retrieved from the Internet: <http://www.cqconcepts.com/inc/inc_chem2_calciumchloride.html>; 2 pgs.

Ferrell and Koshbaten, "Responses of blood vessels in the rabbit knee to electrical stimulation of the joint capsule," 1994 *Antimicrobial Agents and Chemotherapy* 389(5):973-980.

* cited by examiner

Biotin

BIOTIN-FACILITATED TRANSPORT IN GRAM NEGATIVE BACTERIA

This application is a U.S. National Stage of International Application No. PCT/US2004/037896, filed Nov. 12, 2004, which claims the benefit of U.S. Provisional Application Ser. No. 60/519,100, filed Nov. 12, 2003, both of which are incorporated herein by reference in its entirety.

BACKGROUND OF THE INVENTION

The outer membrane of Gram negative bacteria functions as a molecular sieve and allows only very small molecules to passively diffuse into the cell. Porins in the outer membrane allow the transport of larger molecules and may be specific or non-specific in their molecular recognition. Non-specific porins such as Omp F, Omp C and Pho E allow the rapid passage of hydrophilic molecules. Other porins allow the transport of specific molecules. The peptide permeases, for example, have a specificity for oligopeptides. The uptake of oligopeptides is dependent upon size, hydrophobicity and charge.

It is well documented that *Escherichia coli* can not take up large peptides and that the size exclusion limit for porin mediated peptide transport is 650 Daltons or the size of a penta- or hexapeptide. The size exclusion limit for peptide uptake in other Gram negative organisms such as *Salmonella typhimurium* has also been determined and found to be similar to that of *E. coli* (Payne, 1980, "Transport and utilization of peptides by bacteria," p. 211-256. In J. W. Payne (ed.), Microorganisms and Nitrogen Sources. John Wiley & Sons, Chisester; Payne et al., 1994, Adv. Microb. Physiol. 36:1-80). In contrast to Gram negative bacteria, Gram positive bacteria can transport much larger peptides. For example, *Lactococcus lactis* has been shown to take up peptides over 18 residues in length or 2,140 daltons in size (Detmers et al., 1998, Biochemistry 37:16671-16679) while *Bacillus megaterium* can transport molecules up to 10,000 daltons in size (Scherrer et al., 1971, J. Bacteriol. 107:718-735).

Pathogenic Gram negative bacteria represent a serious threat to public health. The American Medical Association and the Centers for Disease Control and Prevention have become increasingly concerned about the dramatic increase in drug-resistance pathogens. The data below shows the incidence of Gram negative drug-resistant pathogens is the most problematic, totaling 59.9% of all drug-resistant pathogens that are monitored.

TABLE I

Incidence of antimicrobial-resistant pathogens that are monitored by the CDC.

| Antimicrobial-resistant pathogen | Number of cases | Percent of total |
|---|---|---|
| Methicillin-resistant *Staphylococcus aureus* (MRSA) | 49,247 | 14.3% |
| Methicillin-resistant coagulase-negative *Staphylococci* (MRCNS) | 29,453 | 8.5% |
| Vancomycin-resistant *Enterococcus* spp (VRE) | 36,114 | 10.5% |
| Ceftazidime, ciprofloxacin/ofloxacin, imipenem, piperacillin, or levofloxacin-resistant *Pseudomonas aeruginosa* | 109,165 | 31.6% |
| Ceftazidime, cefotaxime, ceftriaxone, imipenem, or meropenem-resistant *Enterobacter* spp | 17,252 | 5.0% |
| Ceftazidime, cefotaxime, or ceftriaxone-resistant *Klebsiella pneumoniae* | 16,834 | 4.9% |

TABLE I-continued

Incidence of antimicrobial-resistant pathogens that are monitored by the CDC.

| Antimicrobial-resistant pathogen | Number of cases | Percent of total |
|---|---|---|
| Ceftazidime, cefotaxime, ceftriaxone, ciprofloxacin, ofloxacin, or levofloxacin-resistant *Escherichia coli* | 80,729 | 23.4% |
| Cefotaxime/ceftriaxone, or penicillin-resistant *Pnuemococci* | 6,328 | 1.8% |
| TOTAL | 345,122 | 100.0% |

Data compiled from the CDC National Nosocomial Infections Surveillance (NNIS) August 2002 Report of Antimicrobial-Resistant Pathogens in Hospitals.

Thus, despite many medical advances, the need for antibiotics effective against Gram negative bacteria continues to increase. Unfortunately, the current size and specificity limitations on uptake of molecules by Gram negative bacteria present obstacles to the use cellular uptake machinery to deliver compounds of interest, such as antibiotics, to these pathogens. Compounding this problem is the inability of the pharmaceutical industry to readily generate new antibiotics. Pharmaceutical companies have relied on making derivatives of naturally available compounds for several decades now as evidenced by the multiple generations of new antibiotics from drug classes such as penicillins, cephalosporins, and aminoglycosides. There has been increasing interest in the development of novel peptide antibiotics, however research has focused on the development of peptide antibiotics for Gram positive pathogens due to the problem of peptide uptake by Gram negative pathogens.

Expansion of the size and type of molecules that can be taken up by Gram negative bacteria would open the door to numerous additional scientific and medical applications.

SUMMARY OF THE INVENTION

The invention provides a method for biotin-facilitated introduction of a compound into a bacterial cell, preferably a Gram negative bacterial cell. The compound to be introduced into the cell is biotinylated, and the biotinylated compound is contacted with the cell to effect delivery of the compound to the cell. Advantageously, the biotinylated compound can pass through both the inner and outer cell membranes and is delivered to the cytosol of the cell.

The compound delivered to the Gram negative cell according to the invention is not limited. Preferably, the compound includes an antimicrobial compound. Delivery of a peptide or peptidomimetic (naturally occurring or synthetic), preferably a peptide or peptidomimetic having antimicrobial activity against a Gram negative bacterium, is preferred. The method of the invention makes possible the relatively simple and reliable uptake of small, medium and large peptides by Gram negative bacteria, paving the way to discovery, design, testing and use of new peptide antibiotics effective against Gram negative pathogens.

A biotinylated compound can be delivered to any Gram negative bacterial cell capable of transporting biotin from the extracellular environment to the intracellular environment. Examples of Gram negative bacterial cells include cells of the genus *Escherichia*, *Salmonella*, or *Pseudomonas*. Preferably, the Gram negative bacterial cell is a pathogenic cell, and the compound that is delivered to the call includes a therapeutic, diagnostic or imaging agent and/or has antimicrobial activity.

No pretreatment of the bacterial cell is needed prior to introduction of the biotinylated compound. For example, the method can be performed in the absence of a membrane-permeabilizing agent, such as calcium chloride.

The method of the invention optionally includes linking, covalently or noncovalently, a biotin moiety to the compound to yield the biotinylated compound. Preferably, the biotin moiety is covalently linked to the compound, for example through a biotin carboxyl group.

A biotinylated compound, such as a peptide or peptidomimetic, which itself may or may not be bioactive, is optionally conjugated to a second, preferably bioactive, compound, thereby facilitating biotin-facilitated transport of the second compound into the cell. Alternatively or additionally, the biotinylated compound optionally includes a targeting moiety that specifically targets a Gram negative bacterial cell and/or a targeting moiety that specifically targets a host eukaryotic cell. The targeting moiety can take the form of, for example, a receptor ligand or an antibody or fragment thereof.

Biotin-facilitated introduction of a compound into a Gram negative cell can be used to identify a compound having antimicrobial activity. A Gram negative bacterial cell is contacted with biotinylated compound to cause uptake of the biotinylated compound by the cell, and a determination is made as to whether the biotinylated compound has an antimicrobial effect on the cell. For example, the compound may inhibit the growth of the cell, up to and including causing cell death. The invention further encompasses antimicrobial compounds identified according to the screening method, as well as pharmaceutical compositions, methods of making pharmaceutical compositions, and uses thereof for the treatment or prevention of disease in plants and animals, particularly disease caused by Gram negative bacteria.

DETAILED DESCRIPTION OF ILLUSTRATIVE EMBODIMENTS

Figure 1:
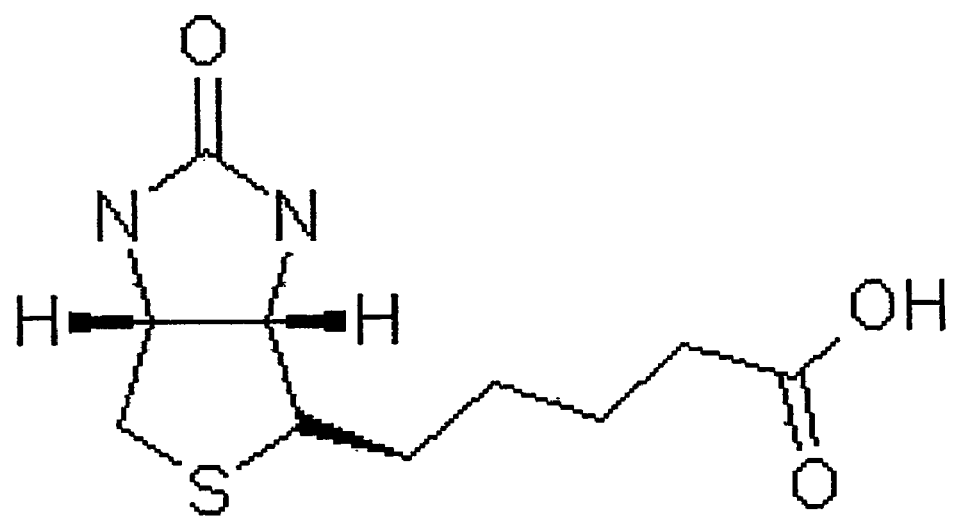
FIG. 1 shows the chemical structure of biotin.

The present invention provides materials and methods for uptake of biotinylated compounds by Gram negative bacteria. The biotin transport system is advantageously be used to accomplish "illicit transport" of biotinylated compounds into Gram negative bacteria. In "illicit transport," the entry of compounds into cells is accomplished through the use of transport systems designed for other substrates, in this case, biotin.

Biotinylated compounds can be transported into any Gram negative bacterium that has the ability to take up biotin from the extracellular environment, for example by passive or active transport through a biotin transporter system. The invention is not limited by the particular biotin transport mechanism used by the Gram negative bacterium. As used herein, the term "biotin transporter" includes one or more components of a biotin transport system that permits the passage of biotin from the extracellular environment, across the cellular membrane(s) and preferably into the cytoplasm of a host cell. For example, a biotin transporter can take the form of one or more membrane-bound biotin receptor molecules or a molecular complex that facilitates uptake of exogenous of biotin by a cell. An example of a microbial biotin transporter is the biotin transporter birB/bioP found in *E. coli*.

A Gram negative bacterium is a bacterium with a cell wall structure that does not retain the methyl violet component of Gram's stain after elution with an organic solvent such as ethyl alcohol. The pink counterstain makes the bacteria appear pink. Gram negative bacteria are characterized by a two cellular membranes separated by a periplasmic space. The periplasmic space is external to the inner, cytoplasmic membrane. On the other side of the periplasm is an outer membrane comprising lipopolysaccharide (LPS) and capsular polysaccharide. Porin proteins typically are present the outer LPS layer. Gram negative bacteria include, without limitation, *Escherichia* spp. (e.g., *E. coli*); *Salmonella* spp. (e.g., *S. typhimurium*); *Pseudomonas* spp. (e.g., *P. aeruginosa*); *Burkholderia* spp.; *Neisseria* spp. (*N. meningitidis*); *Haemophilus* spp. (*H. influenzae*); *Shigella* spp. *Bacterioides* spp.; *Campylobacter* spp.; *Brucella* spp.; *Vibrio* spp.; *Yers-*

*inia* spp.; *Helicobacter* spp.; *Calymmatobacterium* spp.; *Legionella* spp.; *Leptospira* spp.; *Borrelia* spp., *Bordetella* spp.; *Klebsiella* spp.; *Treponema* spp.; *Francisella* spp.; and *Gardnerella* spp. Many of these organisms are known to be pathogenic to animals and/or plants, including mammals such as humans, and can cause diseases and disorders such as enteritis, septicaemia, meningitis, enteric fever, pneumonia, epiglottitis, cellulitis, diarrhea and sexually transmitted diseases.

"Biotinylation" of a compound refers to binding, whether covalent or noncovalent, of a biotin molecule (including an analog or derivative thereof, or other ligand of a biotin transporter) to the compound. Biotinylated compounds as described herein may be singly or multiply biotinylated. When the term "biotin" is used herein, the term includes analogs and derivatives of biotin provided that they also enable or potentiate biotin-facilitated transport into the cell. Biotin analogs are described in U.S. Pat. No. 5,416,016 (Low et al.) and include biocytin, biotin sulfoxide, oxybiotin and other biotin receptor-binding compounds. Other compounds capable of binding to a biotin transporter to initiate biotin-mediated transport of the biotinylated compound include, for example, antibodies specific for the biotin transporter. For example, a compound complexed with an anti-biotin transporter antibody (monoclonal or polyclonal) could be used to initiate transmembrane transport of the complex in accordance with the present invention.

The invention is not limited by the type of compound that is biotinylated and delivered to the Gram negative bacterium, or by the type of linkage between the compound and the biotin. The compound to be delivered may possess a functional group that allows direct covalent or noncovalent linkage to a biotin molecule, or it may be derivatized with a linker or spacer molecule that possesses a functional group thereby allowing indirect covalent or noncovalent linkage of the compound to a biotin molecule. Covalent linkages such as amide, ester or imino bonds between acid, aldehyde, hydroxy, amino, or hydrazo groups on the biotin and the compound to be delivered (or the linker) are preferred.

The functional group on the compound (or the linker molecule) that participates in the linkage with the biotin molecule is preferably one that can form a covalent linkage with the carboxyl group of biotin (FIG. 1). Compounds containing amine groups (either naturally or by way of derivatization with a linker molecule) can be conveniently biotinylated by covalently linking the amine group of the compound to the carboxylic acid of biotin to form an amide bond. However, other conjugation strategies may be used without adversely affecting transmembrane transport of the biotinylated compound. For example, the carboxylic acid of the biotin can be covalently linked to other functional groups on the compound to be biotinylated. Alternatively, the covalent linkage between the biotin and the compound to be biotinylated can include one of the constituents of the biotin ureido ring (nitrogen, sulfur or carbon) or the carbonyl group on the ureido ring.

Well-known biotinylation methods are described in U.S. Pat. No. 5,416,016 (Low et al.). For example, biotinylation can be readily accomplished by activating the carboxyl group of the biotin such that it reacts with free amino groups of the compound to be delivered, such as a peptide or peptidomimetic. A biotinylating reagent such-as D-biotin-N-hydroxysuccinimide ester or biotinyl-p-nitrophenyl ester can be used. The activated ester reacts under mild conditions with amino groups to incorporate a biotin residue into the desired molecule. The procedure to be followed for biotinylating macromolecules using D-biotin-N-hydroxy-succinimide ester is well known in the art (Hofmann et al., J. Am. Chem. Soc. 100, 3585-3590 (1978)). Procedures suitable for biotinylating an exogenous molecule using biotinyl-ϵ-nitrophenyl ester as a biotinylating reagent are also well known in the art (Bodanszk et al., J. Am. Chem. Soc, 99, 235 (1977)). Other reagents such as D-biotinyl-ϵ-aminocaproic acid N-hydroxy-succinimide ester in which ϵ-aminocaproic acid serves as a spacer link to reduce steric hindrance can also be used for the purposes of the present invention.

As an example of a noncovalent linkage, hydrogen bonding between a biotinylated oligonucleotide and a complementary region on a nucleic acid to be delivered can be used to deliver the nucleic acid to a cell.

The term "compound" as used herein is not limited to a single molecule but can include a complex of molecules, ions, and the like, including but not limited to heterogeneous or homogeneous multimolecular complexes, conjugates, chelated or caged complexes, and the like. Compounds whose transport into Gram negative bacteria can be facilitated by derivatization with a biotin moiety include, for example, biomolecules such as polypeptides, nucleic acids, carbohydrates and lipids.

Polypeptides represent a class of compounds that is particularly amenable to transport through the biotin transporter. A polypeptide is a plurality of -amino acids joined together in a linear chain via peptide bonds. The term "polypeptide" is inclusive of the terms peptide, oligopeptide and polypeptide. The amino acids present in a polypeptide or peptide may include naturally occurring amino acids as well as other, non-naturally occurring amino acids or derivatives thereof such as 3-hydroxyproline, 4-hydroxyproline, homocysteine, 2-aminoadipic acid, 2-aminopimelic acid, -carboxyglutamic acid, -carboxyaspartic acid, ornithine, homoarginine, N-methyl lysine, dimethyl lysine, trimethyl lysine, 2,3-diaminopropionic acid, 2,4-diaminobutyric acid, homoarginine, sarcosine, hydroxylysine, substituted phenylalanines, norleucine, norvaline, 2-aminooctanoic acid, 2-aminoheptanoic acid, statine, -valine, naphthylalanines, substituted phenylalanines, tetrahydroisoquinoline-3-carboxylic acid, and halogenated tyrosines.

It should be understood that the terms "peptide" or "polypeptide" do not connote a specific length of a polymer of amino acids, nor are they intended to imply or distinguish whether the polypeptide is produced using recombinant techniques, chemical or enzymatic synthesis, or is naturally occurring. As the term is commonly used in the art, a "peptide" may have between 2 and about 50 or more amino acids, although peptides larger than about 50 amino acids in length are often referred to as polypeptides or proteins. For purposes of the present invention, the term "peptide" is not limited to any particular number of amino acids. Preferably a peptide contains a quantity of amino acids that ranges from 2, 3, 4, 5, 8, 10, or 20 amino acids as a lower size limit, to 30, 40, 50, 60, 70, 80, 90 or 100 amino acids as an upper size limit, and any combination thereof. In various embodiments, the peptide contains, for example, between 2 and 80 amino acids; between 2 and 70 amino acids; between 2 and 50 amino acids; between 2 and 40 amino acids; between 5 and 80 amino acids; between 5 and 70 amino acids; between 5 and 50 amino acids; between 5 and 40 amino acids; between 10 and 80 amino acids; between 10 and 70 amino acids; between 10 and 50 amino acids; between 10 and 40 amino acids; and so on.

As used herein, the terms "polypeptide" and "peptide" include naturally occurring or synthetic peptides, as well as analogs and conjugates thereof. An "analog" of a peptide is one that has been modified by the addition, substitution, or deletion of one or more contiguous or noncontiguous amino acids, or that has been chemically or enzymatically modified, e.g., by attachment of a reporter group, by an N-terminal, C-terminal or other functional group modification or derivatization, or by cyclization, as long as the analog retains the biological activity of the peptide. An analog can thus include additional amino acids at one or both of the termini of a polypeptide. As another example, a polypeptide can be acetylated, acylated, methylated, thiolated, esterified, or conjugated to another molecule.

A peptidomimetic is a polymeric compound that is based on the structure of a parent peptide. However, a peptidomimetic contains non-peptidic structural elements. For example, the backbone of a peptidomimetic may contain one or more nonpeptide bonds. Additionally or alternatively, one or more of the monomeric components of a peptidomimetic may be a component other than a naturally occurring -amino acid. For example, a peptidomimetic can include, without limitation, one or more D-amino acids or one or more other nonnaturally occurring monomeric components such as 3-hydroxyproline, 2-aminopimelic acid and dimethyl lysine, and the like as exemplified above. A peptidomimetic "mimics" a "peptide"; that is, it is capable of mimicking or antagonizing the biological action(s) of a reference peptide, such as a natural parent peptide. As set forth in "Glossary of Terms used in Medicinal Chemistry, a publication of the International Union of Pure and Applied Chemistry (IUPAC) (IUPAC Recommendations 1998), a peptidomimetic may be lacking in one or more classical peptide characteristics such as enzymatically scissile peptidic bonds. (Pure Appl. Chem. 70:1129-1143, 1998). For example, in a peptidomimetic, one or more peptide (amide) bonds in a polypeptide backbone may be replaced by another type of chemical bond, or the backbone atoms of carbon or nitrogen may be substituted by other backbone atoms. A peptidomimetic may be designed de novo, or it may represent a structure that is derived, by substitution, deletion, and or addition, from a parent peptide. However, it should be understood the term peptidomimetic does not include a naturally occurring polypeptide, or a polypeptide that is composed exclusively of naturally occurring -amino acids joined by peptide bonds.

In a preferred embodiment, the compound that is biotinylated and delivered to the Gram negative bacterium is a bioactive compound, preferably a bioactive peptide or peptidomimetic. A bioactive compound is a compound having a biological activity and/or detectability when delivered to a cell. A bioactive compound may directly or indirectly affects the structure or function of a target molecule, such as a component of a cell to which it is delivered. A bioactive compound may be capable of modulating or otherwise modifying cell function and includes pharmaceutically active compounds such therapeutic agents. Bioactive compounds also include diagnostic agents such as imaging agents, which associate with cell components and allow detection, classification and/or quantification. Additional bioactive compounds that can be biotinylated and delivered according to the invention are described in U.S. Pat. No. 5,416,016 (Low et al.). They include without limitation organic molecules including natural products and toxins, metal-containing complexes, molecules containing radioisotopes, dyes and contrast agents, and the like.

Examples of preferred bioactive compounds include antimicrobial peptides and drugs, particularly these effective against pathogenic Gram negative bacteria. Antimicrobial compounds are compounds that adversely affect a microbe such as a bacterium, virus, protozoan, or the like. Antimicrobial compounds include, for example, inhibitory compounds that slow the growth of a microbe, microbiocidal compounds that are effective to kill a microbe (e.g., bacteriocidal and virocidal drugs, sterilants, and disinfectants), and compounds effective to interfere with microbial reproduction, host toxicity, or the like. Compounds that are toxic to Gram negative bacteria, such as antibiotics, membrane-disrupting agents, nucleotide/nucleoside analogs, cytotoxic agents and the like, are particularly important candidates for delivery to Gram negative bacteria according to the invention. Such toxic compounds may arrest or inhibit the growth of the Gram negative bacteria, or may cause cell death.

It should be understood that the term "bioactivity" as used herein includes, without limitation, any type of interaction with another biomolecule, such as a protein, glycoprotein, carbohydrate, for example an oligosaccharide or polysaccharide, nucleotide, polynucleotide, fatty acid, hormone, enzyme, cofactor or the like, whether the interactions involve covalent or noncovalent binding. Bioactivity further includes interactions of any type with other cellular components or constituents including salts, ions, metals, nutrients, foreign or exogenous agents present in a cell such as viruses, phage and the like, for example binding, sequestration or transport-related interactions, as further described in U.S. Pat. No. 5,416, 016 (Low et al.).

Bioactivity of a compound can be detected, for example, by observing phenotypic effects in a host cell in which it is expressed, or by performing an in vitro assay for a particular bioactivity, such as affinity binding to a target molecule, alteration of an enzymatic activity, or the like.

Biotinylated peptides or peptidomimetics may themselves be bioactive and/or they can be conjugated to a bioactive "cargo" compound such as a therapeutic, diagnostic or imaging agent. Conjugation of a "cargo" compound to a biotinylated peptide or peptidomimetic facilitates delivery of the bioactive "cargo" compound to Gram negative bacteria. The compound that is conjugated to the peptide can be any type of compound. Conjugation can take the form of a covalent or noncovalent linkage; preferably it is covalent. For example, the cargo molecule or complex may contain an avidin or streptavidin moiety that binds with the biotin on the biotinylated peptide or peptidomimetic. In that embodiment, multiply biotinylated peptides or peptidomimetics are preferred so that biotin moieties are available for interaction with the cell's biotin transport system in order to facilitate uptake by the cell.

The biotin-facilitated transport mechanism of the invention can be advantageously employed to reliably target and deliver known and newly discovered drugs to Gram negative bacteria via biotinylation of the drug. In some instances, biotin-mediated transport can serve as a secondary membrane transport system for a bioactive compound that already makes use of a different transmembrane transport system, thereby increasing efficacy by improving delivery to the target cell. In other instances, the bioactive compound can contain a targeting moiety that is specific for Gram-negative bacteria, in addition to a biotin moiety for facilitated transport once the compound is in contact with the cell membrane. The term "targeting moiety" is not limited to a particular molecular feature but can include a functional group or larger moiety, or a separate molecular structure that is covalently or noncovalently linked to the bioactive compound. For example, a targeting moiety may include a particular cell surface receptor ligand (e.g., a peptide or small organic molecule), or an antibody or fragment thereof that is capable of specific interaction with a component on the surface of a Gram negative bacterium.

The method of the invention involves contacting a biotinylated compound with a Gram negative bacterium that possesses a biotin transporter for a time sufficient to allow binding of the biotin moiety to the transporter and uptake of the biotinylated compound. Contact between the biotinylated compound and the Gram negative bacterium may be in vitro, as in cell culture, or in vivo. The present invention thus finds diagnostic, prognostic and therapeutic application in both the medical and veterinary fields, as well as application in basic and applied scientific research. For in vitro applications, the number of biotin transporters in a cell membrane can be increased by growing the cells on biotin-deficient substrates to promote biotin transporter production, or by expression of an inserted heterologous gene encoding the biotin transporter.

It should be understood that the method of the invention is effective to transport a biotinylated compound into the cytoplasm of a Gram negative bacterium. That is, the method is effective to cause the biotinylated compound to cross both the outer and inner membranes as well as the periplasmic place separating them. The inner membrane does not act as a barrier to transport and the biotinylated compound typically does not accumulate in the periplasmic space. Rather, significant amounts of the biotinylated compound are transported into the cytosol of the cell. Amounts of the biotinylated compound may be found associated with either or both cell membranes as well, or with the periplasmic space. Notably, it is not necessary to pretreat cells prior to effecting biotin-facilitated transport of a compound of interest. For example, it is not necessary to make cells "competent" for transfer by pretreating in them with a permeabilizing agent such calcium chloride to facilitate transport of a compound, such as a nucleic acid or a protein; indeed the method is preferably performed in the absence of agents such as calcium chloride.

The addition of glucose during biotin-meditated transport can increase the efficiency of transport. Thus, in a preferred embodiment, the biotinylated compound is contacted to the Gram negative bacterial cell in the presence of glucose, preferably about 0.05% to about 0.5% by weight; more preferably about 0.2±0.1% by weight.

Also provided by the invention is a method for screening candidate compounds for bioactivity, particularly antimicrobial activity directed against the host Gram negative bacterium. The method involves contacting a candidate compound, which has been biotinylated, with a Gram negative bacterial cell to cause uptake of the biotinylated compound by the cell. A determination is then made as to whether the compound has antimicrobial activity. One exemplary method for determining whether a compound has antimicrobial activity is to observe whether it has an inhibitory effect on cell growth. As the phrase is used herein, an "inhibitory effect" on cell growth is inclusive of both bacteriocidal activity (i.e., killing/destroying of the bacterial cell) and bacteriostatic activity (i.e., inhibition of the growth and/or multiplication of bacteria without necessarily destroying the bacteria). Inhibition of cell growth can be evidenced, for example, by a reduction in cell doubling time, morphological changes, or a slowing down of the metabolism of the cells, up to and including a cytotoxic effect (cell death). For example, an inhibitory effect on cell growth can be observed as a slowing down or reduction of turbidity of a growing cell culture. Other methods of determining antimicrobial effect are well known to the art. These methods may vary with the type of compound being screened.

The invention is intended to encompass antimicrobial compounds identified according to the biotin-facilitated screening method set forth herein. Such antimicrobial compounds include the biotinylated form of an antimicrobial compound thus identified as well as the antimicrobial compound in a form that does not include a biotin moiety. The compounds identified according to the screening method may be known to the art, or they may be newly discovered as part of a random or nonrandom screening process. These antimicrobial compounds are especially useful to treat or prevent disease caused by Gram negative bacteria, particularly to treat disease caused by a bacterium that served as the bacterial host used in the screening method to identify the antimicrobial compounds.

The invention also provides pharmaceutical compositions and medicaments that include antimicrobial compounds identified according to the biotin-facilitated screening method of the invention, and a pharmaceutically acceptable carrier. Additionally, the invention includes use of the antimicrobial compound for preparation of a pharmaceutical composition or medicament for treatment of a disease caused by a Gram negative bacterium. The antimicrobial compounds are preferably peptides and peptidomimetics. As discussed above, the therapeutically active antimicrobial compound may or may not be biotinylated. Preferably, the antimicrobial compound is biotinylated to facilitate cellular uptake of the antimicrobial compound.

Optionally, the antimicrobial compound used in the pharmaceutical composition of medicament, or administered to a patient, further includes a targeting moiety that is specific for Gram negative bacteria. Incorporation of a moiety targeting a Gram negative bacterium may, in some instances, lessen or eliminate uptake of the antimicrobial compound by other cells in the host, which may in turn increase the effectiveness of the treatment, especially where the microbial infection is extracellular (i.e., present outside the eukaryotic host cells).

It may also be desirable to include in the antimicrobial compound, either additionally or alternatively, a targeting moiety that targets a eukaryotic host cell, including a selected host cell, tissue or organ. Targeting a eukaryotic host cell (or a specific type of cell, tissue, organ, etc.) may be particularly useful in instances where the Gram negative bacterium is an intracellular pathogen and is therefore primarily present inside the animal or plant host cells.

The pharmaceutical composition is administered to a patient in an amount effective to produce the intended diagnostic or therapeutic effect. Medical and veterinary uses are contemplated. The patient is preferably an animal, more preferably a human or a domesticated animal, including a pet or a farm animal, such as a cat, dog, horse, pig, chicken, and the like. In a particularly preferred embodiment, the patient is a human.

The compounds identified according to the screening method of the invention can also be administered to plants, such as agricultural and crop plants, to treat or prevent infection by Gram negative bacteria that are pathogenic to plants. Preferably, such compounds are identified using a Gram negative plant pathogen as the host cell in the screening process.

Pharmaceutical compositions of the invention are administered to a subject in a variety of forms adapted to the chosen route of administration. The formulations include those suitable for oral, rectal, vaginal, topical, nasal, ophthalmic or parenteral (including subcutaneous, intramuscular, intraperitoneal and intravenous) administration. Treatment can be prophylactic or, alternatively, can be initiated after known exposure to an pathogenic bacterium.

The formulations may be conveniently presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier, a finely divided solid carrier, or both, and then, if necessary, shaping the product into the desired formulations.

Formulations of the present invention suitable for oral administration may be presented as discrete units such as tablets, troches, capsules, lozenges, wafers, or cachets, each containing a predetermined amount of the antimicrobial compound as a powder or granules, as liposomes containing the antimicrobial compound, or as a solution or suspension in an aqueous liquor or non-aqueous liquid such as a syrup, an elixir, an emulsion or a draught. The amount of antimicrobial compound in such therapeutically useful compositions is such that the dosage level will be effective to reduce, ameliorate or eliminate the bacterial infection in the subject, preferably by causing the bacterial death.

Formulations suitable for parenteral administration conveniently comprise a sterile aqueous preparation of the antimicrobial compound, or dispersions of sterile powders comprising the antimicrobial compound, which are preferably isotonic with the blood of the recipient. Isotonic agents that can be included in the liquid preparation include sugars, buffers, and sodium chloride. Solutions of the antimicrobial compound can be prepared in water, optionally mixed with a nontoxic surfactant. Dispersions of the antimicrobial compound can be prepared in water, ethanol, a polyol (such as glycerol, propylene glycol, liquid polyethylene glycols, and the like), vegetable oils, glycerol esters, and mixtures thereof. The ultimate dosage form is sterile, fluid and stable under the conditions of manufacture and storage. The necessary fluidity can be achieved, for example, by using liposomes, by employing the appropriate particle size in the case of dispersions, or by using surfactants. Sterilization of a liquid preparation can be achieved by any convenient method that preserves the bioactivity of the antimicrobial compound, preferably by filter sterilization. Preferred methods for preparing powders include vacuum drying and freeze drying of the sterile injectable solutions. Subsequent microbial contamination can be prevented using various antimicrobial agents, for example, antibacterial, antiviral and antifungal agents including parabens, chlorobutanol, phenol, sorbic acid, thimerosal, and the like. Absorption of the antimicrobial compounds over a prolonged period can be achieved by including agents for delaying, for example, aluminum monostearate and gelatin.

Nasal spray formulations comprise purified aqueous solutions of the antimicrobial compound with preservative agents and isotonic agents. Such formulations are preferably adjusted to a pH and isotonic state compatible with the nasal mucous membranes. Formulations for rectal or vaginal administration may be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations comprise the antimicrobial compound dissolved or suspended in one or more media such as mineral oil, petroleum, polyhydroxy alcohols or other bases used for topical pharmaceutical formulations. The compound of the invention is particularly suited to incorporation into topical treatments for wound healing.

In addition to the aforementioned ingredients, the formulations of this invention may further include one or more accessory ingredients including diluents, buffers, binders, disintegrants, surface active agents, thickeners, lubricants, preservatives (including antioxidants) and the like.

Also provided by the invention is a method for treatment of a disease which is treatable by an antimicrobial compound identified using the screening method of the invention. Preferably the antimicrobial compound is a peptide or a peptidomimetic. A therapeutically effective amount of the compound is administered to a subject suffering from, or who is or may have been exposed to, a treatable disease. Treatable diseases preferably include those caused by a pathogenic Gram negative bacterium, and include, for example, enteritis, septicaemia, meningitis, enteric fever, pneumonia, epiglottitis, cellulitis, diarrhea and sexually transmitted diseases as described above. Plant diseases caused by Gram negative bacteria can also be treated.

EXAMPLES

The present invention is illustrated by the following examples. It is to be understood that the particular examples, materials, amounts, and procedures are to be interpreted broadly in accordance with the scope and spirit of the invention as set forth herein.

Example I

Biotinylation Facilitates the Uptake of Large Peptides by *E. coli* and Other Gram Negative Bacteria Gram negative bacteria such as *Escherichia coli* can normally only take up small peptides less than 650 Daltons, or five to six amino acids, in size. This study provides evidence that large biotinylated peptides can be readily transported into Gram negative bacteria such as *E. coli*. We have found that biotinylated peptides up to 31 amino acids in length can be taken up by *E. coli* and that uptake is dependent on the biotin transporter. Uptake could be competitively inhibited by free biotin or avidin, blocked by the protonophore carbobyl cyanide m-chlorophenylhydrazone (CCCP), and was abolished in *E. coli* mutants that lacked the biotin transporter. Biotinylated peptides could be used to supplement the growth of a biotin auxotroph and the transported peptides were shown to be localized to the cytoplasm in cell fractionation experiments. The uptake of biotinylated peptides was also demonstrated for two other Gram negative bacteria, *Salmonella typhimurium* and *Pseudomonas aeruginosa*. This finding may make it possible to create new peptide antibiotics that can be used against Gram negative pathogens. Researchers have used various moieties to cause the illicit transport of compounds in bacteria and this study demonstrates the illicit transport of the largest known compound to date.

Materials and Methods

Bacterial strains. *E. coli* MG1655 (wild-type F-λ-), *E. coli* S1036 (Δbio61 bioP98 (up promoter) recA1 thi rpsL λ b515 b519 galq6 red270 cI857), *E. coli* S1039 (birBts13 Δbio61 bioP98 (up promoter) recA1 thi rpsL λ b515 b519 galq6 red270 cI857), *E. coli* SA291 (rpsL his Δ(gal-chlA)), *Pseudomonas aeruginosa* ATCC9721, *S. typhimurium* LT2, and *S. aureus* ATCC25923 were the bacterial strains used in this study. *E. coli* S1036 and S1039 were derived from SK121 which is a derivative of SK98 (Ketner et al., 1975, Proc. Natl. Acad. Sci. USA 7:2698-2702) and contains a mutation in the λ prophage that enables SK121 to grow at 43° C.

Media. Rich LB and minimal M9 media as described by Miller (Miller, 1972, Experiments in Molecular Genetics. Cold Springs Harbor Laboratory Press, Cold Springs Harbor, N.Y.) was used for *E. coli* MG 1655 and *S. typhimurium* cultures. Rich LB and minimal media as described by Gilleland et al. (Gilleland, Jr., et al., 1974, J. Bacteriol. 117:302-311) was used for *P. aeruginosa*. Tryptic soy broth and minimal media as described by Mah et al. (Mah et al., 1967, Appl.

Microbiol. 15:866-870) was used for *S. aureus*. Rich LB and minimal media as described by Campbell (Campbell, 1961, Virology 14:22-32) was used for *E. coli* S1036, S1039 and SA291. Glucose was the carbon source used in the minimal media for the uptake experiments except for the fractionation studies where maltose was used instead.

Peptides and reagents. The randomized biotinylated peptides XXXX[KBtn]XXXXA (10 amino acids) (SEQ ID NO. 1) and XXXXXXXXXXXXXXX[Kbtn]XXXXXXXXXXXXXXA (31 amino acids) (SEQ ID NO. 2) were synthesized by Sigma Genosys, where A denotes the L-amino acid alanine, X denotes an equimolar mixture of all 20 natural L-amino acids, and KBtn denotes the L-amino acid lysine to which biotin has been attached. The average molecular weight of the 10 and 31 amino acid peptides were determined to be 1,534 and 3,904 Daltons, respectively, using an Applied Biosystems Voyager System 1105 mass spectrometer. This was in very close agreement with the theoretical molecular weights for the 10 and 31 amino acid peptides which were 1,517 and 3,947 Daltons, respectively. Biotin, thiamine, avidin, and bovine serum albumin were purchased from Sigma. NeutrAvidin Horseradish Peroxidase Conjugate and SuperSignal West Dura Extended Duration Chemiluminescent Substrate were purchased from Pierce.

Uptake assays. Minimal 37° C. overnights were diluted into fresh minimal media and incubated at 37° C. until they reached an $OD_{550}$ of 0.5. The 10 and 31 amino acid randomized biotinylated peptides were added to the media at a concentration of 1 μg per mL of culture. After addition of the peptide to the culture, 1 mL aliquots were extracted at time intervals up to an hour, washed twice of extracellular peptide using fresh minimal media, then boiled with SDS-PAGE gradient sample buffer. Samples were run on a 10-16% tricine gradient gel (Schägger et al., 1987, Anal. Biochem. 166:368-379) and transferred to nitrocellulose membranes. The resulting Western blots were treated with NeutrAvidin Horseradish Peroxidase Conjugate and SuperSignal West Dura Extended Duration Chemiluminescent Substrate. The membranes were incubated for 5-10 minutes then exposed to X-ray film for 1-10 minutes. Bands on the film were quantified using the AlphaEase 5.5 Densitometry ProGram from Alpha Innotech.

To test the effects that biotin, thiamine, avidin, BSA, or CCCP had on peptide uptake, these compounds were added to mid-log cultures five minutes before the addition of the biotinylated peptide. One mL samples were extracted 10 minutes after the addition of the peptide and analyzed by SDS PAGE as previously described.

Figure 2:
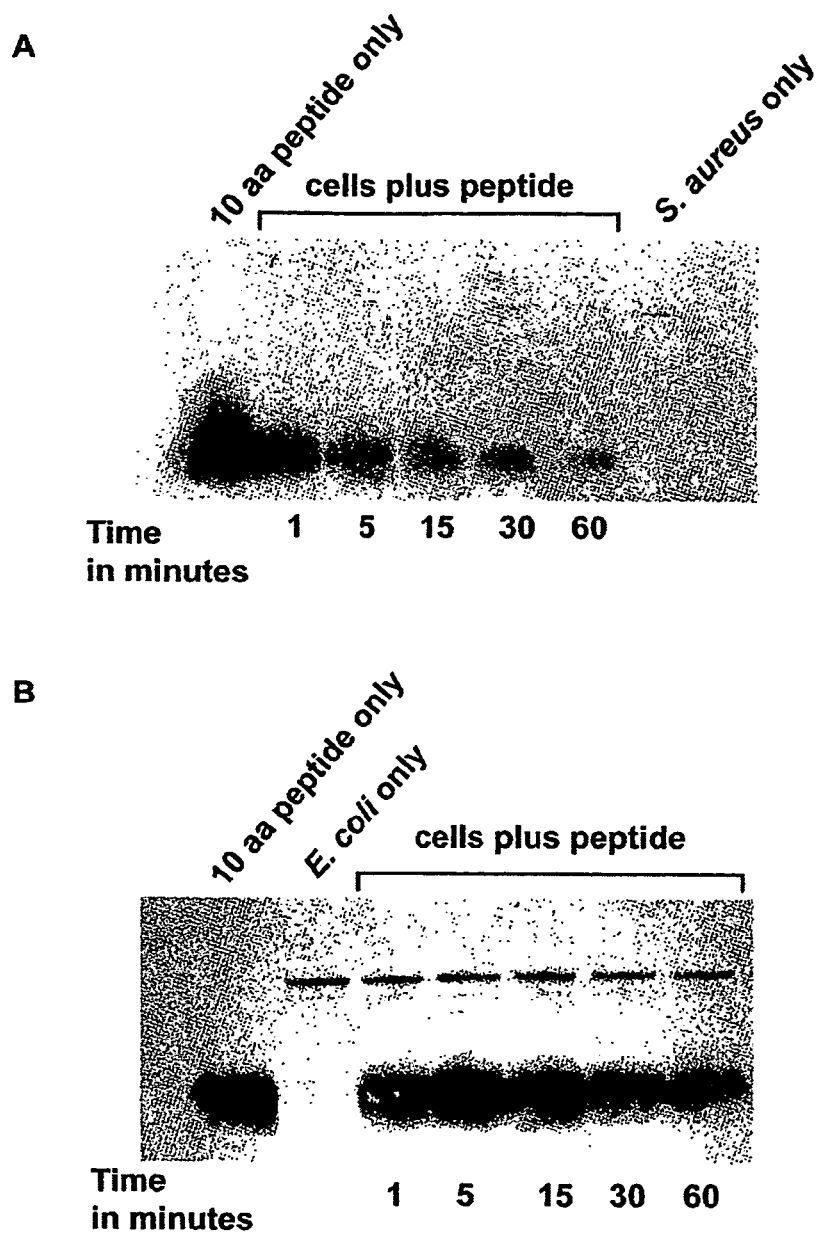
FIG. 2 shows uptake of a 10 amino acid (aa) biotinylated peptide by (A) *S. aureus* and (B) *E. coli* MG1655 (B). The biotinylated peptide was added to mid-log cultures, samples were taken at different time intervals and analyzed by sodium dodecyl sulfate polyacrylamide gel electrophoresis (SDS PAGE) as described in Example I. Peptide-only and cell-only samples were included as controls.
Figure 3:
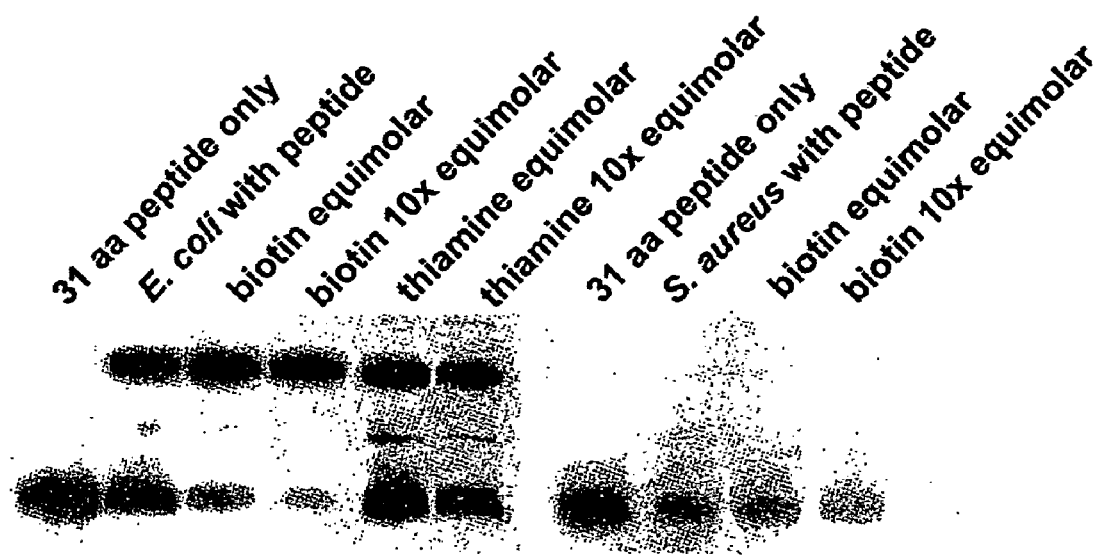
FIG. 3 shows the effect of biotin on the uptake of a 31 amino acid (aa) biotinylated peptide in *E. coli* and *S. aureus*. Biotinylated peptide and equimolar or 10× equimolar amounts of biotin or thiamine were added to mid-log cultures. The cell samples were processed and analyzed by SDS PAGE as described in Example 1.
Figure 4:
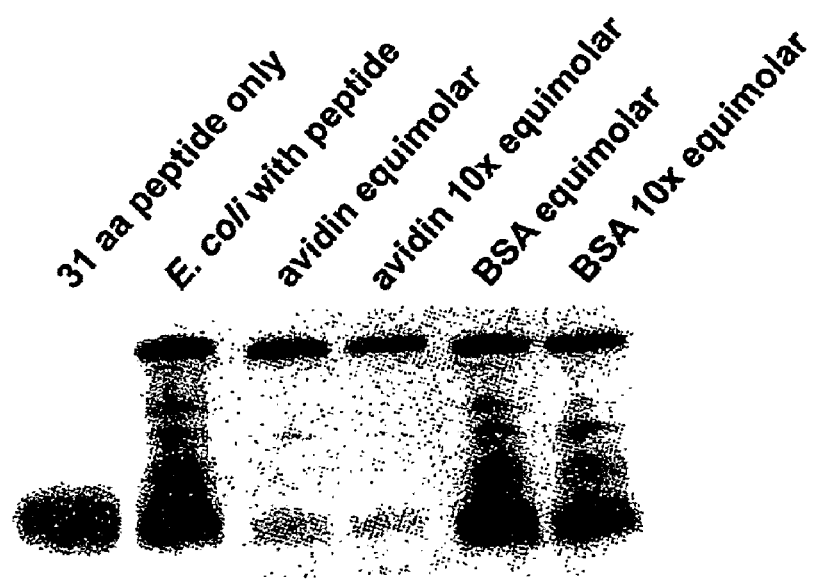
FIG. 4 shows the effect of avidin on the uptake of a 31 amino acid (aa) biotinylated peptide in *E. coli*. Biotinylated peptide and equimolar or 10× equimolar amounts of avidin or bovine serum albumin were added to mid-log cultures. The cell samples were processed and analyzed by SDS PAGE as described in Example 1.
Figure 8:
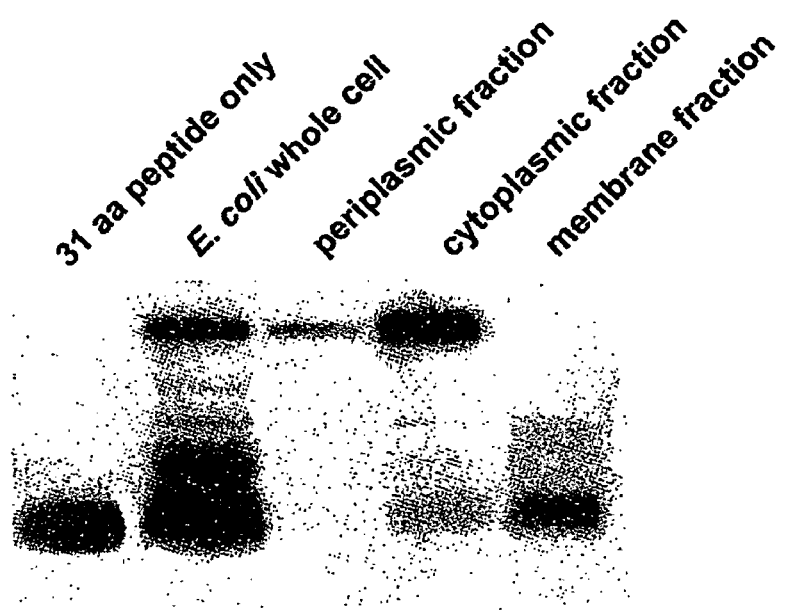
FIG. 8 shows localization of the biotinylated peptide in *E. coli*. Biotinylated peptide was added to mid-log cultures of MG1655 and the cells were fractionated into periplasmic, cytoplasmic, and membrane samples and analyzed by SDS PAGE as described in Example I. Peptide-only and whole cell plus peptide samples were included as controls.
Figure 9:
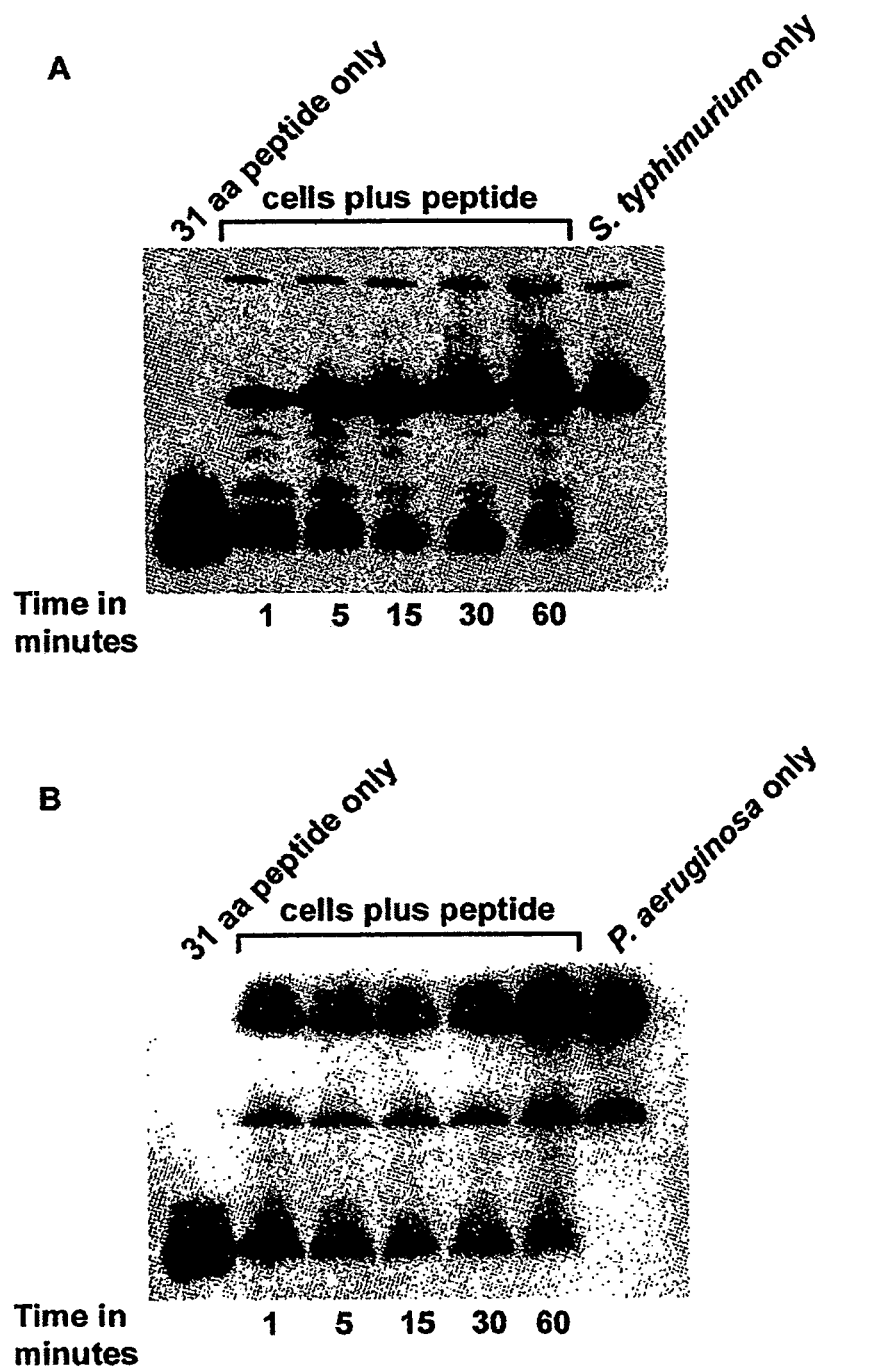
FIG. 9 shows uptake of a 31 amino acid biotinylated peptide by (A) *S. typhimurium* and (B) *P. aeruginosa*. Biotinylated peptide was added to mid-log cultures, aliquots were taken at different time intervals and analyzed by SDS PAGE as described in Example I. Peptide-only and cell-only samples were included as controls.

An upper 22,500 Dalton protein band can be seen in the western blots involving *E. coli* samples that are shown in FIGS. 2, 3, 4, 5, 6 and 8. This band is from the *E. coli* biotin carboxyl carrier protein which is the prominent biotinylated protein in *E. coli* (Fall et al. 1975, Biochim. Biophys. Acta 379:496-503). Multiple upper bands can be seen in the western blots involving *S. typhimurium* and *P. aeruginosa* samples that are shown in FIG. 9. Most bacteria contain several biotinylated proteins and the multiple biotinylated bands seen in the western blots involving *S. typhimurium* and *P. aeruginosa* are consistent with this fact. Additional protein bands ranging from 22,500 to 4,000 Daltons can be seen in the blots involving *E. coli* samples that are shown in FIGS. 4 and 8. These two blots were exposed to film longer than the other blots that are shown in FIGS. 2, 3, 5, 6 and 8, and these extra bands are likely extraneous background bands which appear due to overdevelopment of the blot. The biotinylated peptides in FIGS. 2 and 9 disappear over time. This is due to degradation by peptidases and proteases that are present in bacterial cells (Walker et al., 2003, J. Peptide Res. 62:214-226) All studies were repeated in triplicate, however, only one representative western blot is shown for each experiment.

Cell fractionation. The 31 amino acid biotinylated peptide was added to *E. coli* MG1655 cells that had been grown to an $OD_{550}$ of 0.5 in minimal maltose media to allow for the induction of the maltose binding protein which served as one of the fractionation controls. After an additional 10 minutes of incubation, the cultures were then subjected to periplasmic shock as described by Ames et al. (Ames et al., 1984, J. Bacteriol. 160:1181-1183) to isolate the periplasmic fraction. The remaining cell pellet was then further fractionated using the method described by Altman et al. (1983, J. Bacteriol. 155:1130-1137) to prepare cytoplasmic and membrane fractions with one modification. Cytoplasmic proteins were precipitated by adding trichloroacetic acid at a final concentration of 5% w/v to the cytoplasmic fraction. The precipitate was then centrifuged at 4° C., 50,000 rpm for 30 minutes to pellet the cytoplasmic proteins. The periplasmic, cytoplasmic, and membrane samples were analyzed using a 10-16% tricine gradient gel and Western blotted as described above for the uptake assays.

Results

Biotinylated peptides up to 31 amino acids in length can be taken up by *E. coli*. We initially tested the ability of *E. coli* and *S. aureus* to import a 10 amino acid biotinylated peptide. Randomized peptides were used as opposed to peptides with a specific sequence in order to avoid nonspecific uptake that might be caused by certain amino acid sequences. Peptide was added to mid-log cultures of bacteria which were allowed to incubate for time intervals up to 60 minutes in duration. Samples were removed at specific times, pelleted, washed to remove any peptide in the media that had not been taken up by the cells, and then analyzed as described above.

As shown in FIG. 2, both *E. coli* and *S. aureus* readily imported the 10 amino acid biotinylated peptide. Using densitometry, we determined that up to 75% of the peptide was imported within the first 5 minutes of incubation. To determine whether the import, which was arguably due to biotinylation in *E. coli*, was limited to smaller peptides, we also tested whether a much larger 31 amino acid biotinylated peptide could be imported in *E. coli* and *S. aureus*. As with the 10 amino acid biotinylated peptide, the 31 amino acid biotinylated peptide was also taken up by both *E. coli* and *S. aureus* (data not shown).

The uptake of biotinylated peptides in *E. coli* can be competitively inhibited by biotin or avidin and blocked by the protonophore CCCP. Given that peptides larger than six amino acids cannot be taken up by *E. coli*, the obvious interpretation of our results was that biotin was the mechanism by which this unexpected uptake was occurring. To test this assumption, we conducted a competition experiment in both *E. coli* and *S. aureus* using biotin. We rationalized that since large peptides can be readily taken up by Gram positive bacteria such as *S. aureus*, biotin should have no competitive effect. However, in *E. coli*, if the uptake was due to biotin, then free biotin should be able to competitively block uptake. FIG. 3 shows that this is indeed the case. The uptake of biotinylated peptides could be blocked in *E. coli* by the addition of biotin whereas biotin had no effect on the uptake of biotinylated peptides in *S. aureus*.

Additionally, we showed that the competitive inhibition in *E. coli* was specific to biotin and the use of another similarly sized vitamin, thiamine, had no effect. Because avidin is known to tightly bind biotin (Gilleland, Jr., et al., 1974, J. Bacteriol. 117:302-311), we also tested whether avidin would be able to competitively inhibit the uptake of biotinylated peptides in *E. coli*. FIG. 4 shows that avidin could competitively inhibit the uptake of biotinylated peptides in *E. coli*, but that the use of another similarly sized protein, bovine serum albumin, which is routinely used in in vitro studies, had no effect.

Figure 5:
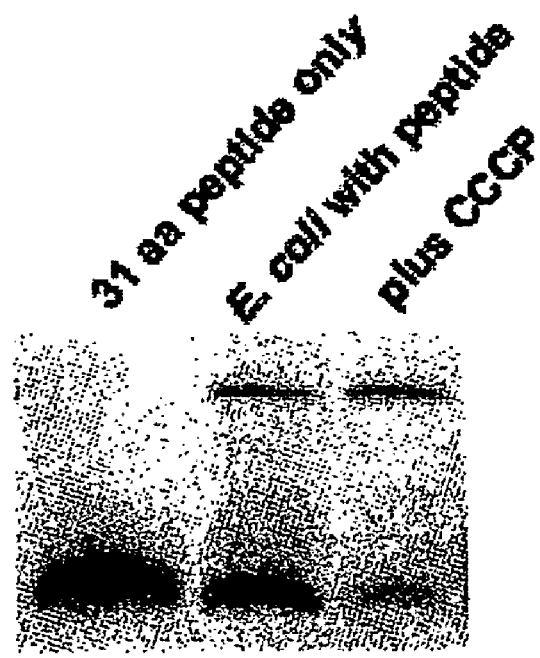
FIG. 5 shows the effect of carbonyl cyanide m-chlorophenylhydrazone (CCCP) on the uptake of a 31 amino acid biotinylated peptide in *E. coli*. CCCP was added at a final concentration of 50 µM to mid-log cultures of MG1655 since it has been shown that *E. coli* continues to grow normally at this concentration of CCCP (Kinoshita et al., 1984, J. Bacteriol. 160:1074-1077). The cell samples were processed and analyzed by SDS PAGE as described in Example I.

It has been shown that biotin uptake is blocked by the protonophore CCCP which disrupts membrane potential in *E. coli* (Piffeteau et al., 1982, Biochim. Biophys. Acta 688:29-36; Piffeteau et al., 1985, Biochim. Biophys. Acta 816:77-82). If the uptake of biotinylated peptides was due to the biotin transport system, then CCCP would be expected to block the uptake of biotinylated peptides. FIG. 5 shows that uptake is blocked when CCCP is added prior to the addition of the biotinylated peptide.

Figure 6:
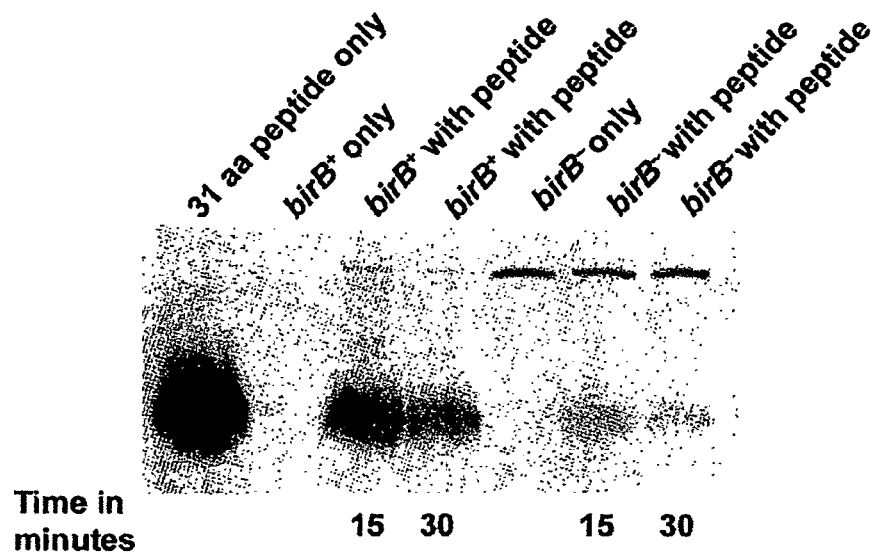
FIG. 6 shows the effect of a birB⁻ mutation on the uptake of a 31 amino acid (aa) biotinylated peptide in *E. coli*. The biotinylated peptide was added to mid-log cultures of birB⁺ and birB⁻ cells. After 10 minutes of incubation the cell samples were processed and analyzed by SDS PAGE as described in Example I. Peptide-only and cell-only samples were included as controls.

The uptake of biotinylated peptides in *E. coli* is dependent on the biotin transport system. The biotin transport system in *E. coli* has been well characterized and mutants that prevent the uptake of biotin, birB/bioP, are available (Campbell et al., 1980, J. Bacteriol. 142:1025-1028; Eisenberg et al., 1975, Bacteriol. 122:66-72). If the import of biotinylated peptides in *E. coli* were indeed due to the biotin transport system, then birB mutants should not be able to take up biotinylated peptides. FIG. 6 shows that this is the case. A wild-type birB$^+$ strain was able to take up biotinylated peptide, while an isogenic birB$^-$ mutant strain was not.

Figure 7:
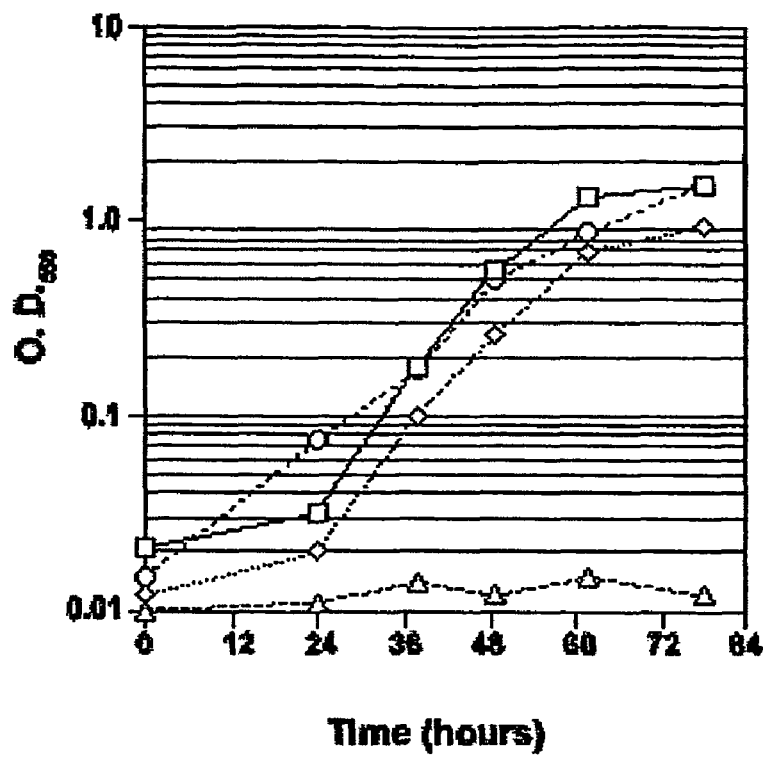
FIG. 7 shows growth of an *E. coli* bio auxotroph on minimal media supplemented with biotin or equimolar amounts of biotinylated peptides. The *E. coli* SA291 bio auxotrophic strain was grown in minimal media at 37° C. with either no supplement (Δ), 1 µg/mL biotin (□), or equimolar amounts of the 10 (○) and 31 (◊) amino acid biotinylated peptides. Aliquots were removed at 12 hour intervals and the $OD_{550}$ was determined.

Biotinylated peptides can be used to fulfill the growth requirements of an *E. coli* biotin auxotroph. To further demonstrate that biotinylated peptides were truly taken up by *E. coli*, we tested whether a biotinylated peptide could be used instead of biotin to fulfill the growth requirement of an *E. coli* biotin auxotroph in minimal media. FIG. 7 shows that an *E. coli* biotin auxotroph grows as well in media supplemented with biotinylated peptide as it does in media supplemented with biotin.

Cell fractionation studies show that the biotinylated peptide can be detected in the cytoplasm of *E. coli*. To demonstrate biochemically that biotinylated peptides were taken up by *E. coli*, we performed cell fractionation studies where periplasmic, cytosolic, and membrane fractions were prepared from cultures to which biotinylated peptide had been added. FIG. 8 shows that the biotinylated peptide localized to both the cytoplasmic and membrane fractions. Of the peptide that could be detected, 66% was found in the membrane fraction and 34% was found in the cytoplasmic fraction. To verify that the cell fractionation studies had been done correctly, we used the same cell fractions to visualize the GroEL and MBP proteins which are known to localize to the cytoplasm and periplasm, respectively. GroEL was found primarily in the cytoplasmic fraction, while MBP was found primarily in the periplasmic fraction. GroEL's distribution was 93% in the cytoplasm and 7% in the membrane, while MBP's distribution was 95% in the periplasm, 3% in the membrane and 2% in the cytoplasm (data not shown).

Biotinylated peptides can be taken up by other Gram negative bacteria. Given our findings in *E. coli*, we also wanted to test whether biotinylated peptides could be transported by other Gram negative bacteria. We found that both the 10 and 31 amino acid biotinylated peptides could be readily transported by both *S. typhimurium* and *P. aeruginosa*. FIG. 9 shows the uptake of the 31 amino acid biotinylated peptide by *S. typhimurium* and *P. aeruginosa*.

Discussion

While conducting an in vivo screen for randomly encoded peptides which could inhibit the growth of *Staphylococcus aureus*, we performed a test to confirm that potential peptides resulting from the screen would be readily taken up, as expected, by this Gram positive organism. The synthetic peptides had been biotinylated so they could be easily visualized on Western blots using a neutravidin horseradish peroxidase conjugate. A biotinylated 10 amino acid peptide was added extracellularly to growing cultures of *S. aureus* and an *E. coli* control, since it is well established that Gram negative bacteria such as *E. coli* can only take up very small peptides that are six amino acids or less in size. The *E. coli* control therefore should not have been able to take up the 1,534 dalton peptide. Surprisingly, we found that the peptide was taken up by both *S. aureus* and *E. coli* within 5 minutes of incubation. This observation appeared to contradict the known size exclusion limit of *E. coli* and suggested that the biotinylation of peptides may allow for peptide uptake to occur via the biotin transport system.

In this study, we have shown that biotinylation can indeed facilitate the uptake of peptides up to 31 amino acids in length by *E. coli* and that transport is dependent on the biotin transporter, birB/bioP. We have found that the uptake of the biotinylated peptides can be competitively inhibited by free biotin or avidin, and blocked by the protonophore CCCP which disrupts membrane potential. We also demonstrated that biotinylated peptide could be used to supplement the growth of a biotin auxotroph and that the biotinylated peptide was localized to the cytoplasm in cell fractionation studies. What is known about biotin function in *E. coli* is consistent with our finding that biotin can be used to facilitate the uptake of peptides via the biotin transporter in *E. coli*.

Biotin can be synthesized as well as transported by *E. coli* and the genes involved in biotin biosynthesis and transport are repressible by biotin (Guha, 1971, J. Mol. Biol. 56:53-62). Biotin's transport system is regulated independently of the biosynthetic pathway (Pai, 1973, J. Bacteriol. 116:494-496). *E. coli* readily imports the vitamin biotin when it is available and concomitantly represses biotin synthesis. Biotin uptake is specific, energy dependent, and can accumulate against a concentration gradient (Piffeteau et al., 1982, Biochim. Biophys. Acta 688:29-36; Piffeteau et al., 1985, Biochim. Biophys. Acta 816:77-82; Prakash et al., 1974, J. Bacteriol. 120: 785-791). Maximum uptake is observed during exponential growth phase and glucose has been shown to increase biotin uptake slightly. The rate of biotin uptake has also been shown to increase proportionally to the amount of extracellular biotin that is available.

The first mutant that affected biotin transport was discovered by Campbell et al. (1972, Proc. Nat. Acad. Sci. USA 69:676-680). They termed the mutant bir for biotin retention and showed that the mutant abolished the ability of *E. coli* to take up biotin. Eisenberg et al. (1975, Bacteriol. 122:66-72) isolated an independent mutant that abolished biotin uptake which they termed bioP. Campbell et al. (1980, J. Bacteriol. 142:1025-1028) renamed their original bir mutant birB and showed that birB and bioP mutants were identical via genetic mapping experiments.

It is surprising that the biotin transport system can be used to facilitate the uptake of large peptides. Biotin has a molecular weight of 244, making it relatively small in comparison to a 10 amino acid biotinylated peptide with an average molecular weight of 1,534 or a 31 amino acid biotinylated peptide with an average molecular weight of 3,904. Clearly the biotin uptake system must be flexible since it can accommodate larger molecules. Our finding that 34% of the biotinylated peptide localized to the cytoplasm and 66% of the peptide localized to the membrane is consistent with such a model. Some of the biotinylated peptide was able to completely pass through the biotin transporter while a significant fraction remained in the membrane.

There is contradictory evidence with regard to how biotin's structure affects its ability to be taken up by *E. coli*. Prakash and Eisenberg (Prakash et al., 1974, J. Bacteriol. 120:785-791) stated that while the ureido ring of biotin must be intact for uptake, modification of the side chain has little effect. However, Piffeteau et al. (Piffeteau et al., 1982, Biochim. Biophys. Acta 688:29-36) suggested that modifications to the side chain of biotin could drastically affect biotin's ability to be transported and that the carboxyl group on the side chain is essential for biotin uptake. In the biotinylated peptides used in this study, the biotin carboxyl group is joined to the amino group of lysine via an amide bond and thus the carboxyl group of biotin is not available for recognition. This fact supports Prakash and Eisenberg's argument that the side chain of biotin does not affect uptake. Extrapolation from our data further suggests that it is indeed the ureido ring that is important for recognition and uptake.

The fact that biotinylation can facilitate the uptake of very large peptides by Gram negative bacteria represents the illicit transport of the largest known compound to date. Illicit transport has been defined as the entry of compounds into cells through the use of transport systems designed for other substrates (Ames et al., 1973, Proc. Natl. Acad. Sci. USA 70:456-458). There are numerous examples of the use of peptide permeases to facilitate the uptake of small antibacterial peptides or antibiotics that have been coupled to di- or tripeptides (Ames et al., 1973, Proc. Natl. Acad. Sci. USA 70:456-458; Atherton et al., 1980, Antimicrob. Agents Chemother. 18:897-905; Fickel et al., 1973, Nat. New Biol. 241:161-163; Morely et al., 1983, Biochem. Soc. Trans. 11:798-800; Staskawicz et al., 1980, J. Bacteriol. 142:474-479). Additionally, researchers have used various siderophores that are involved in iron uptake to facilitate the transport of antibiotics (Luckey et al., 1972, J. Bacteriol. 111:731-738; Wittmann et al., 2002, Bioorg. Med. Chem. 10:1659-1670). All of these compounds are much smaller than the 10 and 31 amino acid peptides that we have found to be transported via biotinylation.

Interestingly, biotinylated molecules are currently being investigated for drug delivery in mammalian cells. Avidin drugs that bind to biotinylated vectors are being used to promote delivery across the blood brain barrier (Bonfils et al., 1992, Bioconjug. Chem. 3:277-284; Pardridge, 2002, Arch. Neurol. 59:3540; Song et al., 2002, J. Pharmacol. Exp. Ther. 301:605-610) while antitumor toxins or imaging agents coupled to streptavidin are being delivered using biotinylated antibodies (Hussey et al., 2002, J. Am. Chem. Soc. 124:6265-6273; Press et al., 2001, Blood 98:2535-2543). Biotinylation has also been shown to promote the delivery of polyethylene glycol camptothecin conjugates into human ovarian carcinoma cells (Minko et al., 2002, Cancer Chemother. Pharmacol. 50:143-50) and increase the cellular uptake of polyethylene glycol TAT nonapeptide conjugates into human Caco and CHO cells (Ramanathan et al., 2001, J. Control. Release 77:199-212).

Our finding that biotinylated peptides can be taken up by Gram negative bacteria such as *E. coli, S. typhimurium* and *P. aeruginosa*, represents an intriguing possibility for the development of antibacterial peptides. Given the abundance of naturally occurring antibacterial peptides and the increased interest in designing new synthetic peptide drugs, researchers have been trying to develop novel peptide antibiotics that can inhibit the function of key intracellular targets identified through genomics. Researchers have been focusing on Gram positive bacteria where the uptake of large peptides is not problematic. The use of biotinylated peptides may make it possible to use this same approach to develop antibacterial peptides that can target Gram negative bacteria.

The complete disclosures of all patents, patent applications including provisional patent applications, and publications, and electronically available material (e.g., GenBank amino acid and nucleotide sequence submissions) cited herein are incorporated by reference. The foregoing detailed description and examples have been provided for clarity of understanding only. No unnecessary limitations are to be understood therefrom. The invention is not limited to the exact details shown and described; many variations will be apparent to one skilled in the art and are intended to be included within the invention defined by the claims.

What is claimed is:

1. A method for introducing a compound into a Gram negative bacterial cell, the method comprising contacting the cell, in the absence of a membrane-permeabilizing agent, with a biotinylated compound, wherein the compound comprises a peptide and wherein the contact is effective to deliver the compound into the cytosol of the cell.

2. A method for introducing a compound into a Gram negative bacterial cell, the method comprising contacting the cell, in the absence of a membrane-permeabilizing agent, with a biotinylated compound, wherein the contact is effective to deliver the compound into the cytosol of the cell.

3. A method for identifying a compound having antimicrobial activity comprising:
   contacting a Gram negative bacterial cell, in the absence of a membrane-permeabilizing agent, with biotinylated compound to cause uptake of the biotinylated compound into the cytosol of the cell;
   determining whether the biotinylated compound has an antimicrobial effect on the cell.

4. The method of claims 2 or 3 wherein the compound comprises a peptide.

5. The method of any of claims 1, 2 or 3 further comprising linking a biotin moiety to the compound to yield the biotinylated compound.

6. The method of claim 1 wherein the peptide is conjugated to first and second bioactive compounds, wherein the first bioactive compound comprises biotin.

7. The method of any of claims 1, 2 or 3 wherein the Gram negative bacterial cell is a cell of the genus *Escherichia, Salmonella*, or *Pseudomonas*.

8. The method of claim 7 wherein the Gram negative bacterial cell is an *E. coli* cell, a *S. typhimurium* cell, or a *P. aeruginosa* cell.

9. The method of any of claims 1, 2 or 3 wherein the Gram negative bacterial cell comprises a biotin transporter.

10. The method of claim 9 where the biotin transporter comprises a birB/bioP transporter.

11. The method of any of claims 1, 2 or 3 wherein the compound comprises a therapeutic, diagnostic or imaging agent.

12. The method of claim 11 wherein the compound further comprises a targeting moiety that specifically targets a Gram negative bacterial cell.

13. The method of claim 12 wherein the targeting moiety comprises a receptor ligand or an antibody or fragment thereof.

14. The method of claim 11 wherein the compound comprises an antibiotic.

15. The method of any of claims 1, 2 or 3, wherein the Gram negative bacterial cell is a pathogen.

16. The method of any of claims 1, 2 or 3 wherein the compound, when introduced into the cell, inhibits the growth of the cell.

17. The method of any of claims 1, 2 or 3 wherein the compound, when introduced into the cell, causes the death of the cell.

18. The method of any of claims 1, 2 or 3 performed in the absence of calcium chloride.

* * * * *

UNITED STATES PATENT AND TRADEMARK OFFICE
CERTIFICATE OF CORRECTION

PATENT NO.         : 7,601,511 B2                                    Page 1 of 1
APPLICATION NO. : 10/579248
DATED              : October 13, 2009
INVENTOR(S)        : Altman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 93 days.

Signed and Sealed this

Fifth Day of October, 2010

David J. Kappos
*Director of the United States Patent and Trademark Office*